(12) United States Patent
DeSa

(10) Patent No.: US 7,092,085 B1
(45) Date of Patent: Aug. 15, 2006

(54) SAMPLE HOLDER WITH INTENSE MAGNETIC FIELD

(76) Inventor: Richard J. DeSa, 1540 Ethridge Rd., Jefferson, GA (US) 30549

( * ) Notice: Subject to any disclaimer, the term of this patent is extended or adjusted under 35 U.S.C. 154(b) by 322 days.

(21) Appl. No.: 10/760,808

(22) Filed: Jan. 20, 2004

(51) Int. Cl.
*G01N 1/10* (2006.01)
*G01J 3/28* (2006.01)

(52) U.S. Cl. .................. 356/246; 356/326; 324/321
(58) Field of Classification Search ........ 356/364–368, 356/244, 246, 440, 318, 327, 326; 324/313, 324/318, 321, 307; 250/225
See application file for complete search history.

(56) References Cited

U.S. PATENT DOCUMENTS

| | | | |
|---|---|---|---|
| 3,205,764 A | 9/1965 | Letter | |
| 3,442,592 A | 5/1969 | Grosjean | |
| 3,552,865 A | 1/1971 | Leung et al. | |
| 3,635,678 A | 1/1972 | Seitz et al. | |
| 3,695,772 A | 10/1972 | Spyropoulos | |
| 3,740,151 A | 6/1973 | Chaney et al. | |
| 3,801,204 A | 4/1974 | Jennings et al. | |
| 3,869,214 A | 3/1975 | Egli et al. | |
| 4,670,003 A * | 6/1987 | Moroz | 494/10 |
| 4,725,140 A | 2/1988 | Musha | |
| 4,818,881 A | 4/1989 | Tanton et al. | |
| 5,635,889 A | 6/1997 | Stelter | |
| 5,706,087 A | 1/1998 | Thompson et al. | |
| 5,838,444 A | 11/1998 | Jo | |
| 6,046,804 A | 4/2000 | Kawamura et al. | |
| 6,573,817 B1 | 6/2003 | Gottschalk et al. | |
| 6,593,743 B1 * | 7/2003 | de Swiet et al. | 324/318 |
| 2005/0017720 A1 * | 1/2005 | Mett et al. | 324/321 |

FOREIGN PATENT DOCUMENTS

JP    02003329562 A  * 11/2003

OTHER PUBLICATIONS

Jasco Model J-810 Spectropolarimeter specifications sheet with attached ECS Technical Report No. 31 (dated Jan. 2001) to the optional permanent magnet accessory (PM-409 and PM-410) Shows limited magnetic field strength of 0.4-0.7 T.

* cited by examiner

*Primary Examiner*—Hoa Q. Pham
(74) *Attorney, Agent, or Firm*—Patricia Smith King

(57) ABSTRACT

The present invention is directed to a sample holder that generates an intense magnetic field for inducing a signal proportional to the magnetic field in a molecular sample while enabling the simultaneous exposure of the sample to one or more measurement light beams. The body of the sample holder consists of a permanent magnet means for producing the intense magnetic field at a strength sufficient to induce the signal. The holder fits in the palm of a user's hand and enables manual manipulation of the holder by the user. A sample chamber and a beam channel are present in the sample holder. Versions of the holder are disclosed which orient the magnetic lines of flux parallel or perpendicular to the sample so as to induce MCD or MLD signals, respectively.

15 Claims, 3 Drawing Sheets

SAMPLE HOLDER WITH INTENSE MAGNETIC FIELD

CROSS-REFERENCES

Not applicable.

STATEMENT REGARDING FEDERALLY SPONSORED RESEARCH OR DEVELOPMENT

Not applicable.

BACKGROUND

Exposure of molecules to intense magnetic fields will induce signals (e.g., magnetic circular dichroism, magnetic linear dichroism, magnetic optical rotatory dispersion, and the like) which may augment the information gained by their spectrometric analysis. The problem lies in providing a sample holder with means of generating a magnetic field of sufficient intensity to induce measurable signals in a sample, while simultaneously minimizing its size, weight and expense.

A magnetic circular dichroism (MCD) signal is the differential absorption of left and right circularly polarized light induced in a molecular sample by an externally applied, intense magnetic field. MCD signal can augment the information provided by the measurement of absorption of a sample using ordinary light. Many biologically important molecules exhibit particularly strong MCD signals which can be detected even when present in complex mixtures. MCD measurements require the magnetic field be oriented parallel (or anti-parallel) to the direction of the measurement light beam (or beams).

Magnetic fields oriented perpendicularly to the direction of the measurement beam may produce a magnetic linear dichroism (MLD) signal by partially aligning or orienting large macromolecules and macromolecular arrays. The MLD signal may be used to study biomembranes, phospholipid membranes and other molecular constructs.

Information relevant to attempts to provide a magnetic field capable of inducing magnetic signals in molecular samples can be found in U.S. Pat. No. 3,442,592 to Grosjean; U.S. Pat. No. 3,740,151 to Chaney et al.; U.S. Pat. No. 3,801,204 to Jennings et al.; U.S. Pat. No. 4,725,140 to Musha; U.S. Pat. No. 4,818,881 to Tanton et al.; U.S. Pat. No. 5,838,444 to Jo; U.S. Pat. No. 5,706,087 to Thompson et al.; U.S. Pat. No. 6,046,804 to Kawamura et al.; and, U.S. Pat. No. 6,573,817 to Gottschalk. However, each one of these references suffers from one or more disadvantages discussed as follows.

The most commonly employed types of magnets used to generate magnetic fields are electromagnets which produce up to about 1.5 T (15,000 Gauss). Electromagnets are large and heavy preventing their easy manual manipulation by a user. They also require a large power supply and water-cooling.

Because the magnetic flux must be parallel to the measurement light beam(s) (for measuring MCD or magnetic optical rotatory dispersion (MORD)), long drillings (i.e., up to 50 cm or more) must be made through the pole pieces of the electromagnet to admit the measurement light beam(s), which beam or beams must be painstakingly aligned. The resulting drillings are minimal in diameter and result in a narrow light path which is very difficult to align properly with a single light beam, and generally precludes the use of more than one light beam. These magnets are cumbersome, expensive and difficult to install in a CD, or other type of, spectrometer. Often, the CD instrument itself must be altered to reduce the effects of the stray magnetic signals which are always produced by electromagnets.

Superconducting magnets are also available. However, though they can produce magnetic fields up to 10.0 T (100,000 Gauss), they are large, expensive and require large supplies of cryogenic gases. Their use generally requires specialized laboratories and specially trained personnel to operate them.

A third type of magnet is a permanent magnet which has advantages over the prior two in not requiring a power supply or the use of specialized facilities and personnel. However, the most powerful permanent magnets available today, produce a magnetic field strength of only about 0.7 T (7,000 Gauss) or less, making them generally inadequate to the task of inducing a significant magnetic signal in a molecular sample. The signal induced by a magnetic field in a sample is directly proportional to the field strength of the magnet. Therefore, the field strength should be as high as possible, and should generally exceed 0.7 T (7,000 Gauss) in strength. Further, these other magnets are larger and heavier and therefore difficult to manipulate.

For the foregoing reasons, there is a need for a small manually manipulatable sample holder that enables simultaneous exposure of a molecular sample to one or more beams of light and to an intense magnetic field sufficient to induce a signal in the molecular sample.

SUMMARY

The present invention is directed to an apparatus that satisfies this need. The apparatus is a sample holder that is small and manually manipulatable and that produces an intense magnetic field for inducing a signal in a molecular sample while enabling the simultaneous exposure of the sample to one or more measurement beams.

In one version, the sample holder consists of a block-shaped body with a front face, a back face and four side faces, the side faces comprising a top, a bottom, a left and a right face. The body consists of permanent magnet means for producing the intense magnetic field at a strength sufficient to induce the signal in the molecular sample. The body is of a size and a weight so that the sample holder fits in the palm of a user's hand and enables manual manipulation of the holder by the user. The holder further consists of a sample chamber in which the intense magnetic field is formed. The sample chamber consists of a cavity in the body of the sample holder, the cavity having an aperture at one end and a solid base at the opposing end, and partially penetrating the body from the aperture located on the top face of the body downward toward the opposing bottom face. The cavity is of a size and a shape so that a cuvette containing the molecular sample may be inserted through the aperture to rest on the solid base, thereby exposing the molecular sample to the intense magnetic field upon insertion into the sample chamber. The holder still further consists of a beam channel through which one or more light beams emitted by a spectrometer may pass. The beam channel consists of a hollow channel extending from the front face to the back face of the body in perpendicular orientation to the sample chamber and intersecting the sample chamber at a location above its base. The beam channel further consists of an opening on the front face and an opening on the back face through either of which the one or more light beams may be directed.

The intense magnetic field consists of magnetic lines of flux, which in one version of the sample holder used to measure magnetic circular dichroism (MCD) or magnetic optical rotatory dispersion (MORD) signals, are oriented substantially parallel to the one or more light beams. In another version of the sample holder, the lines of flux are oriented substantially perpendicular to the one or more light beams and this version may be used to induce magnetic linear dichroism (MLD) signals in the sample.

In one version of the sample holder, the strength of the intense magnetic field is substantially at least 1.0 T (10,000 Gauss).

In still another version, the sample holder may further consist of a base upon which the sample holder may rest which may or may not be attached to the spectrometer or other device with which the sample holder is to be used.

Several objects and advantages of the present invention are:

means by which a sample holder is provided that enables the generation of an intense magnetic field sufficient to induce a signal in a molecular sample (e.g., MCD, MORD, MLD), while remaining small and light weight so as to enable a user to easily manually manipulate it;

means by which the magnetic field is provided so as to orient the lines of flux substantially parallel to the one or more light beams to enable the induction of MCD or MORD signals in the sample;

means by which the magnetic field is provided so as to orient the lines of flux substantially perpendicular to the one or more light beams to enable the induction of MLD signals in the sample;

means by which a sample holder is provided that enables a user to quickly and easily manually rotate it 180 degrees so as to reverse the magnetic lines of flux relative to one or more measurement beams;

means by which a beam channel is proportioned to provide a light path which is sufficiently short in length and large in size to enable easy alignment of the beam channel with one or more light beams so as to assure clear passage of the light beam(s) through the beam channel with minimal effort by a user; and, means by which a sample holder is provided that may tolerate a range of sample chamber sizes and shapes to accommodate cuvettes of various pathlengths, while maintaining its ability to generate an intense magnetic field.

The reader is advised that this summary is not meant to be exhaustive. Further features, aspects, and advantages of the present invention will become better understood with reference to the following description, accompanying drawings and appended claims.

BRIEF DESCRIPTION OF DRAWINGS

For a better understanding of the present invention, reference may be made to the accompanying drawings, in which.

DESCRIPTION

Figure 1:
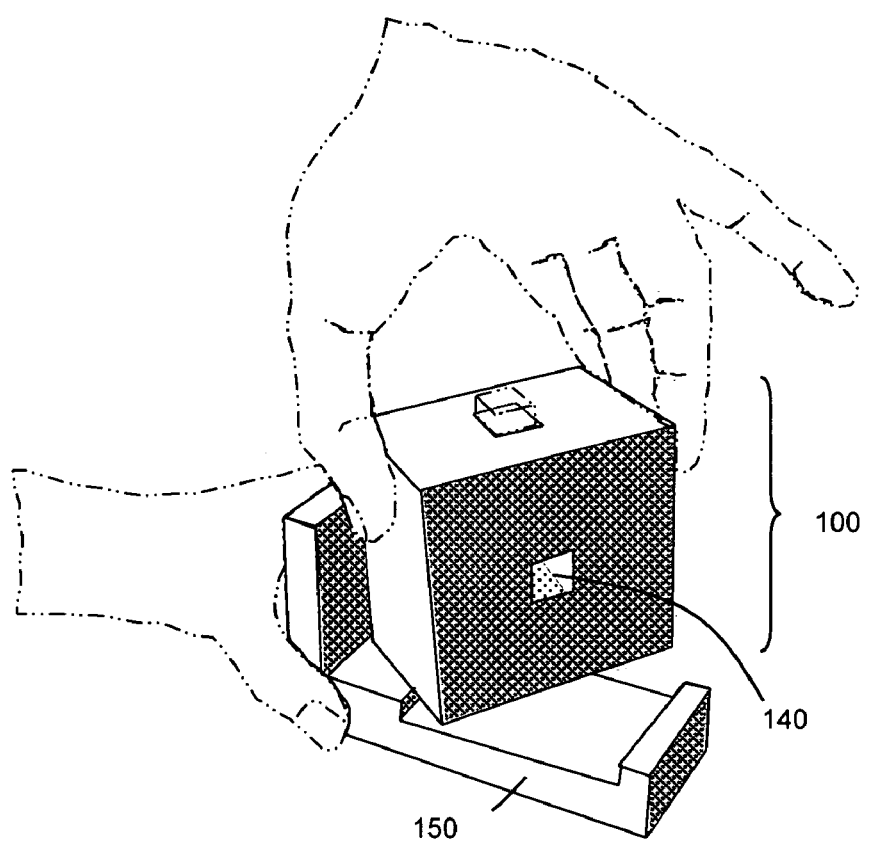
FIG. 1, shows a schematic diagram depicting the sample holder as it may be manually repositioned on a base relative to a light source.

Referring now specifically to the figures, in which identical or similar parts are designated by the same reference numerals throughout, a detailed description of the present invention is given. It should be understood that the following detailed description relates to the best presently known embodiment of the invention. However, the present invention can assume numerous other embodiments, as will become apparent to those skilled in the art, without departing from the appended claims.

It should also be understood that, while the methods disclosed herein may be described and shown with reference to particular steps performed in a particular order, these steps may be combined, sub-divided, or re-ordered to form an equivalent method without departing from the teachings of the present invention. Accordingly, unless specifically indicated herein, the order and grouping of the steps is not a limitation of the present invention.

DEFINITIONS

Achiral molecules—Molecules that are superimposable with their mirror images.

Chiral molecules—Molecules that are not superimposable with their mirror images.

Circular dichroism (abbreviated CD)—CD is the differential absorption of left and right circularly polarized light by a molecular sample.

Dichroism—Dichroism is the property of having different absorption coefficients for light polarized in different directions.

Electromagnet—A magnet consisting of a coil wound around a soft iron or steel core. The core is strongly magnetized when current flows through the coil, and is almost completely demagnetized when the current is interrupted.

Linear dichroism (abbreviated LD)—LD is the differential absorption of left and right linearly polarized light by a molecular sample.

Magnetic circular dichroism (abbreviated MCD)—MCD signal is CD induced in a molecular sample by an externally applied intense magnetic field.

Magnetic flux (a.k.a. magnetic lines of flux; magnetic lines of force)—Lines used to represent the magnetic induction in a magnetic field, selected so that they are parallel to the magnetic induction at each point and so that the number of lines per unit area of a surface perpendicular to the induction is equal to the induction. In the context of the present invention, magnetic flux lines are either oriented parallel (for measurement of MCD) or perpendicular (for measurement of MLD) to the measurement beam(s).

Magnetic linear dichroism (abbreviated MLD)—MLD signal is LD induced in a molecular sample by an externally applied intense magnetic field.

Magnetic optical rotatory dispersion (abbreviated MORD)—MORD signal is ORD induced in a molecular sample by an externally applied intense magnetic field.

Optical rotatory dispersion (abbreviated ORD)—Specific rotation of the plane of polarization of a beam, considered as a function of wavelength.

Permanent magnet (abbreviated PM)—A piece of hardened steel or other magnetic material that has been strongly magnetized and retains its magnetism indefinitely. A dipole permanent magnet is a permanent magnet that is oppositely charged at two poles.

Signal—Any of a number of types of signals induced in a molecular sample by an intense magnetic field. Types of signals may include MCD, MLD, MORD and the like.

Spectrometer—A spectroscope equipped with a photoelectric photometer to measure radiant intensities at various wavelengths.

Spectroscope—An optical instrument consisting of a slit, collimator lens, prism or grating, and a telescope or objective lens which produced a spectrum for visual observation.

Tesla (abbreviated T)—A unit of magnetic induction or magnetic flux density in the meter-kilogram-second system (SI) of physical units. One tesla equals one weber per square meter, corresponding to $10^4$ gauss. It is used in all work involving strong magnetic fields, while the gauss is more useful with small magnets.

DETAILED DESCRIPTION

Figure 2A:
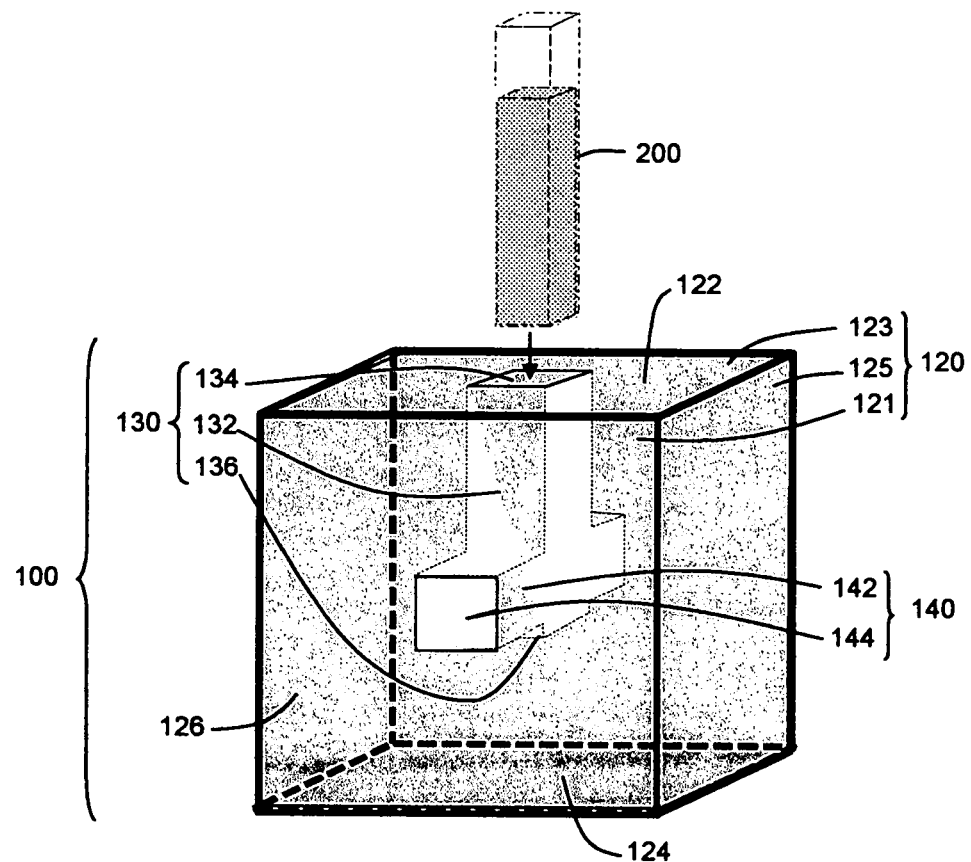
FIG. 2*a*, shows a schematic diagram depicting a version of the sample holder and a cuvette with molecular sample before the sample is placed in the sample chamber of the holder.
Figure 2B:
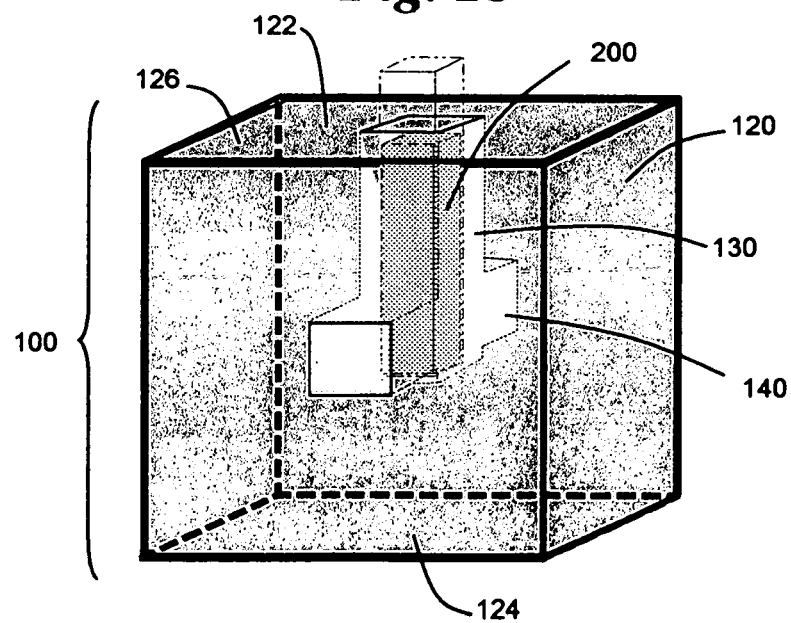
FIG. 2*b*, shows the holder and sample of FIG. 2*a* with the sample positioned in the sample chamber of the holder.
Figure 3A:
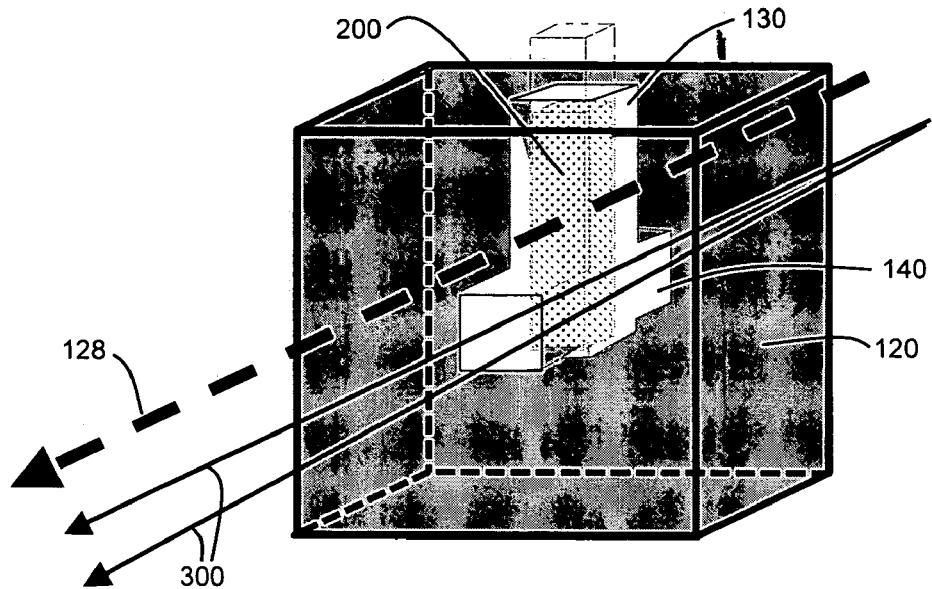
FIG. 3*a*, shows a version of the holder with sample as depicted in FIG. 2*b*, in which the magnetic lines of flux run in parallel orientation to the one or more light beams; and, FIG. 3*b*, shows a version of the holder with sample as depicted in FIG. 2*b*, in which the magnetic lines of flux run in perpendicular orientation to the one or more light beams.
Figure 3B:
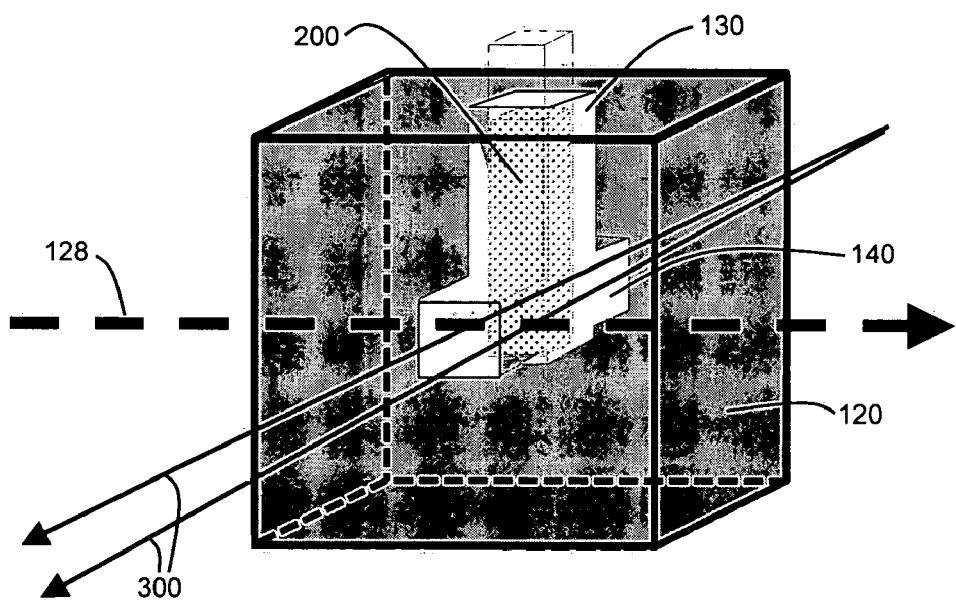

Referring to FIGS. 1 and 2a–b, the present invention is a sample holder 100 with an intense magnetic field for inducing a signal in a molecular sample 200 placed therein. Used in conjunction with a spectrometer, the sample holder 100 enables simultaneous exposure of the molecular sample 200 to both the intense magnetic field and to one or more light beams. Once the one or more light beams pass through the molecular sample 200, the magnetically induced signal(s) are detected by the spectrometer.

The sample holder 100 is depicted in FIG. 1 to show how its size and weight are such as to enable a user to fit it in the palm of the user's hand and to manually manipulate it during use. As shown, an optional base 150 is present upon which the sample holder 100 may be manually manipulated according to the needs of the user, and upon which the sample holder 100 may rest while in use. The base 150 may or may not be attached to the spectrometer. Manual manipulations by the user may include the repositioning of the sample holder 100 on the base 150, the lifting of the holder 100 for easy inspection, moving the holder 100 for use with other equipment, or the like.

The sample holder 100 consists of a block-shaped body 120 which has a front face 121, a back face 122 opposite the front face and four side faces, the side faces comprising a top 123, a bottom 124 opposite the top, a left 125 and a right face 126 opposite the left.

The body 120 is of a size and a weight such that the sample holder fits in the palm of a user's hand and enables manual manipulation thereof by the user. In one version of the sample holder 100, the body is approximately 3"×3" (7.6 cm×7.6 cm) square on its front and back faces (121, 122) and approximately 2" (5.1 cm) in depth, making the side faces (123–126) each approximately 3"×2" (7.6 cm×5.1 cm) in size. The reader will appreciate that this size easily fits in the palm of a user's hand.

Additionally, the weight of the body of the sample holder is low to enable the user to easily pick the sample holder 100 up to move or inspect it, or to transport it for use with another apparatus. In one version of the sample holder 100, the weight is only about 3 pounds.

The body 120 is a permanent magnet means for producing the intense magnetic field at a strength sufficient to induce the signal in the molecular sample 200. The magnetic field strength will be substantially at least 1.0 T (10,000 Gauss). In one embodiment described below, the magnetic field strengths achieved by the present invention are 1.4 T to 1.8 T (14,000–18,000 Gauss). Since the signal induced by a magnetic field in a sample is directly proportional to the field strength of the magnet, the greater the magnetic field strength the stronger the signal. The present invention thereby provides a substantial magnetic field strength enabling significantly strong signals to be induced in a molecular sample.

In one embodiment of the present invention, the permanent magnet means is a customized version of the dipole permanent magnet structure disclosed in U.S. Pat. No. 5,635,889 to Stelter (incorporated herein by reference in its entirety). Magnetic field strengths of between 1.4 T (14,000 Gauss) and 1.8 T (18,000 Gauss) are achievable with this permanent magnet structure, whose total size and weight enable manual manipulation by the user. This particular version of the permanent magnet means further prevents the escape of the lines of magnetic flux from the structure. Interference with sensitive devices is thereby greatly reduced. Also, what little magnetism does escape is temporally constant, further reducing observable interference with the functioning of other devices. Additionally, the permanent magnet means can achieve these high magnetic field strengths while retaining the small size and weight described above.

The reader should note however, that applicant intends to encompass within the language used herein any permanent magnet structure presently existing or developed in the future that performs the same function of producing an intense magnetic field while retaining a small size and weight.

The sample holder 100 further consists of a sample chamber 130 in which the intense magnetic field is formed by the permanent magnet means. The sample chamber 130 consists of a cavity 132 in the body 120 of the sample holder, the cavity 132 having an aperture 134 at one end and a solid base 136 at the opposing end. The cavity 132 partially penetrates the body 120 from the aperture 134 located on the top face 123 of the body downward toward the opposing bottom face 124. The sample chamber 130 may be sized and shaped so that the molecular sample 200 contained in a cuvette 210 (as illustrated in FIGS. 2a–3b), may be inserted through the aperture 134 to rest on the solid base 136. Once inserted into the sample chamber 130, the molecular sample 200 is exposed to the intense magnetic field.

The sample holder 100 still further consists of a beam channel 140 through which one or more light beams 300 emitted by a spectrometer may pass. The beam channel 140 consists of a hollow channel 142 extending from the front face 121 to the back face 122 of the body 120 in perpendicular orientation to the sample chamber 130. The beam channel 140 intersects the sample chamber 130 at a location above its base 136. The beam channel 140 further consists of two openings 144 on the front and back faces (121, 122) through either of which the one or more light beams 300 may be directed.

As mentioned above, the permanent magnet structure of the body 120 of the sample holder 100 induces an intense magnetic field within the sample chamber 130. This magnetic field consists of lines of magnetic flux 128. The permanent magnet structure may be formed to produce lines of magnetic flux 128 that are substantially parallel to the beam channel 140, and thereby the one or more light beams 300 (see FIG. 3a). Alternatively it may be formed to produce lines of magnetic flux 128 that are substantially perpendicular to the beam channel 140, and thereby the one or more light beams 300 (see FIG. 3b).

In the parallel configuration (FIG. 3a), the lines of magnetic flux may induce a magnetic circular dichroism (MCD) signal in the sample 200, or a magnetic optical rotatory dispersion (MORD) signal. Additionally, the small size and weight of the sample holder 100 enables the user to easily rotate it 180 degrees to configure the lines of flux anti-parallel to the one or more light beams 300, to induce a signal for measuring other properties of the sample 200. In the perpendicular configuration (FIG. 3b), the lines of magnetic flux may induce a magnetic linear dichroism (MLD) signal in the sample 200. These various magnetic signals (MCD, MORD or MLD) in turn, modify the one or more beams of light as they pass through the sample 200, and these modifications in the light are then detected and measure by the spectrometer.

ADVANTAGES OF THE INVENTION

The previously described versions of the present invention have many advantages, including:

means by which a sample holder is provided that enables the generation of an intense magnetic field sufficient to induce a significant signal in a molecular sample (e.g., MCD, MORD, MLD), while remaining small and light weight so as to enable a user to easily manually manipulate it;

means by which the magnetic field is provided so as to orient the lines of flux substantially parallel to the one or more light beams to enable the induction of MCD or MORD signals in the sample;

means by which the magnetic field is provided so as to orient the lines of flux substantially perpendicular to the one or more light beams to enable the induction of MLD signals in the sample;

means by which a sample holder is provided that enables a user to quickly and easily manually rotate it 180 degrees so as to reverse the magnetic lines of flux relative to one or more measurement beams;

means by which a beam channel is proportioned to provide a light path which is sufficiently short in length and large in size to enable easy alignment of the beam channel with one or more light beams so as to assure clear passage of the light beam(s) through the beam channel with minimal effort by a user; and, means by which a sample holder is provided that may tolerate a range of sample chamber sizes and shapes to accommodate cuvettes of various pathlengths, while maintaining its ability to generate an intense magnetic field.

The present invention does not require that all the advantageous features and all the advantages need to be incorporated into every embodiment thereof.

CLOSING

Although the present invention has been described in considerable detail with reference to certain preferred versions thereof, other versions are possible. Therefore, the spirit and scope of the appended claims should not be limited to the description of the preferred versions contained herein.

What is claimed is:

1. A sample holder with an intense magnetic field for inducing a signal in a molecular sample, the sample holder comprising:

a body with a front face, a back face and four side faces, the side faces comprising a top, a bottom, a left and a right face, the body comprising a permanent magnet means for producing the intense magnetic field at a strength sufficient to induce the signal in the molecular sample, the body being of a size and a weight such that the sample holder fits in the palm of a user's hand and enables manual manipulation thereof by the user;

a sample chamber in which the intense magnetic field is formed, the sample chamber comprising a cavity in the body of the sample holder, the cavity having an aperture at one end and a solid base at an opposing end, the cavity partially penetrating the body from the aperture located on the top face of the body downward toward the opposing bottom face, the cavity being of a size and a shape so that the molecular sample may be inserted through the aperture to rest on the solid base, thereby exposing the molecular sample to the intense magnetic field upon insertion into the sample chamber; and, a beam channel through which one or more light beams emitted by a spectrometer may pass, the beam channel comprising a hollow channel extending from the front face to the back face of the body in perpendicular orientation to the sample chamber and intersecting the sample chamber at a location above its base, the beam channel further comprising an opening on the front face and an opening on the back face through either of which the one or more light beams may be directed;

whereby a small manually manipulatable sample holder is provided enabling simultaneous exposure of a molecular sample placed therein to an intense magnetic field and to one or more beams of light emitted by a spectrometer, the strength of the intense magnetic field being sufficient to induce a signal in the molecular sample detectable by the spectrometer.

2. The sample holder of claim 1, wherein the strength of the intense magnetic field is substantially at least 1.0 T (10,000 Gauss).

3. The sample holder of claim 1, wherein the intense magnetic field comprises lines of magnetic flux in parallel orientation to the beam channel and, thereby, the one or more light beams, and wherein the signal induced in the molecular sample is a magnetic circular dichroism signal.

4. The sample holder of claim 1, wherein the intense magnetic field comprises lines of magnetic flux in parallel orientation to the beam channel and, thereby, the one or more light beams, and wherein the signal induced in the molecular sample is a magnetic optical rotatory dispersion signal.

5. The sample holder of claim 1, wherein the intense magnetic field comprises lines of magnetic flux in perpendicular orientation to the beam channel and, thereby, the one or more light beams, and wherein the signal induced in the molecular sample is a magnetic linear dichroism signal.

6. The sample holder of claim 1, further comprising a base on which the sample holder sits.

7. A sample holder with an intense magnetic field for inducing a magnetic circular dichroism signal in a molecular sample, the sample holder comprising:

a body with a front face, a back face and four side faces, the side faces comprising a top, a bottom, a left and a right face, the body comprising a permanent magnet means for producing the intense magnetic field at a strength sufficient to induce the magnetic circular dichroism signal in the molecular sample, the body being of a size and a weight such that the sample holder fits in the palm of a user's hand and enables manual manipulation thereof by the user and the intense magnetic field comprising lines of magnetic flux;

a sample chamber in which the intense magnetic field is formed, the sample chamber comprising a cavity in the body of the sample holder, the cavity having an aperture at one end and a solid base at an opposing end, the cavity partially penetrating the body from the aperture located on the top face of the body downward toward the opposing bottom face, the cavity being of a size and a shape so that the molecular sample may be inserted through the aperture to rest on the solid base, thereby exposing the molecular sample to the intense magnetic field upon insertion into the sample chamber; and, a beam channel through which one or more light beams emitted by a spectrometer may pass, the beam channel comprising a hollow channel extending from the front face to the back face of the body in substantially parallel orientation to the magnetic lines of flux and in perpendicular orientation to the sample chamber and intersecting the sample chamber at a location above its base, the beam channel further comprising an opening on the front face and an opening on the back face through either of which the one or more light beams may be directed;

whereby a small manually manipulatable sample holder is provided enabling simultaneous exposure of a molecular sample placed therein to an intense magnetic field and to one or more beams of light emitted by a spectrometer, the strength of the intense magnetic field and orientation of the magnetic lines of flux relative to the one or more beams of light being sufficient to induce a magnetic circular dichroism signal in the molecular sample detectable by the spectrometer.

8. The sample holder of claim 7, wherein the strength of the intense magnetic field is substantially at least 1.0 T (10,000 Gauss).

9. A sample holder with an intense magnetic field for inducing a magnetic linear dichroism signal in a molecular sample, the sample holder comprising:

a body with a front face, a back face and four side faces, the side faces comprising a top, a bottom, a left and a right face, the body comprising a permanent magnet means for producing the intense magnetic field at a strength sufficient to induce the magnetic linear dichroism signal in the molecular sample, the body being of a size and a weight such that the sample holder fits in the palm of a user's hand and enables manual manipulation thereof by the user and the intense magnetic field comprising lines of magnetic flux;

a sample chamber in which the intense magnetic field is formed, the sample chamber comprising a cavity in the body of the sample holder, the cavity having an aperture at one end and a solid base at an opposing end, the cavity partially penetrating the body from the aperture located on the top face of the body downward toward the opposing bottom face, the cavity being of a size and a shape so that the molecular sample may be inserted through the aperture to rest on the solid base, thereby exposing the molecular sample to the intense magnetic field upon insertion into the sample chamber; and, a beam channel through which one or more light beams emitted by a spectrometer may pass, the beam channel comprising a hollow channel extending from the front face to the back face of the body in substantially perpendicular orientation to the magnetic lines of flux and in perpendicular orientation to the sample chamber and intersecting the sample chamber at a location above its base, the beam channel further comprising an opening on the front face and an opening on the back face through either of which the one or more light beams may be directed;

whereby a small manually manipulatable sample holder is provided enabling simultaneous exposure of a molecular sample placed therein to an intense magnetic field and to one or more beams of light emitted by a spectrometer, the strength of the intense magnetic field and orientation of the magnetic lines of flux relative to the one or more beams of light being sufficient to induce a magnetic linear dichroism signal in the molecular sample detectable by the spectrometer.

10. The sample holder of claim 9, wherein the strength of the intense magnetic field is substantially at least 1.0 T (10,000 Gauss).

11. A method for inducing a signal in a molecular sample by exposing the molecular sample to an intense magnetic field, the method comprising:

providing a sample holder, the sample holder comprising:

a body with a front face, a back face and four side faces, the side faces comprising a top, a bottom, a left and a right face, the body comprising a permanent magnet means for producing the intense magnetic field at a strength sufficient to induce the signal in the molecular sample, the body being of a size and a weight such that the sample holder fits in the palm of a user's hand and enables manual manipulation thereof by the user;

a sample chamber in which the intense magnetic field is formed, the sample chamber comprising a cavity in the body of the sample holder, the cavity having an aperture at one end and a solid base at an opposing end, the cavity partially penetrating the body from the aperture located on the top face of the body downward toward the opposing bottom face, the cavity being of a size and a shape so that the molecular sample may be inserted through the aperture to rest on the solid base, thereby exposing the molecular sample to the intense magnetic field upon insertion into the sample chamber; and, a beam channel through which one or more light beams emitted by a spectrometer may pass, the beam channel comprising a hollow channel extending from the front face to the back face of the body in perpendicular orientation to the sample chamber and intersecting the sample chamber at a location above its base, the beam channel further comprising an opening on the front face and an opening on the back face through either of which the one or more light beams may be directed; and, exposing the molecular sample to the intense magnetic field by inserting the molecular sample into the sample chamber, thereby inducing the signal for detection by the spectrometer.

12. The method of claim 11, wherein the strength of the intense magnetic field is substantially at least 1.0 T (10,000 Gauss).

13. The method of claim 11, wherein the intense magnetic field comprises lines of magnetic flux in parallel orientation to the beam channel and, thereby, the one or more light beams, and wherein the signal induced in the molecular sample is a magnetic circular dichroism signal.

14. The method of claim 11, wherein the intense magnetic field comprises lines of magnetic flux in parallel orientation to the beam channel and, thereby, the one or more light beams, and wherein the signal induced in the molecular sample is a magnetic optical rotatory dispersion signal.

15. The method of claim 11, wherein the intense magnetic field comprises lines of magnetic flux in perpendicular orientation to the beam channel and, thereby, the one or more light beams, and wherein the signal induced in the molecular sample is a magnetic linear dichroism signal.

* * * * *